US012788967B2

(12) United States Patent
Bertora et al.

(10) Patent No.: US 12,788,967 B2
(45) Date of Patent: Nov. 10, 2026

(54) BIOMEDICAL DEVICE FOR THE TREATMENT OF ULCERS OR LESIONS

(71) Applicants: Fremslife S.r.l., Genoa (IT); Fondazione Istituto Italiano di Tecnologia, Genoa (IT)

(72) Inventors: Franco Bertora, Genoa (IT); Michele Palermo, Genoa (IT); Luigi Miracoli, Genoa (IT); Marco Contardi, Palermo (IT); Rosalia Bertorelli, Milan (IT); Maria Summa, Novi Ligure (IT); Athanassia Athanassiou, Ceranesi (IT)

( * ) Notice: Subject to any disclaimer, the term of this patent is extended or adjusted under 35 U.S.C. 154(b) by 244 days.

(21) Appl. No.: 18/702,106

(22) PCT Filed: Oct. 14, 2022

(86) PCT No.: PCT/IB2022/059855

§ 371 (c)(1),
(2) Date: Apr. 17, 2024

(87) PCT Pub. No.: WO2023/067449

PCT Pub. Date: Apr. 27, 2023

(65) Prior Publication Data

US 2024/0408381 A1 Dec. 12, 2024

(30) Foreign Application Priority Data

Oct. 18, 2021 (IT) ........................ 102021000026615

(51) Int. Cl.
*A61N 1/04* (2006.01)
*A61N 1/36* (2006.01)
*A61N 1/372* (2006.01)

(52) U.S. Cl.
CPC ......... *A61N 1/0468* (2013.01); *A61N 1/0476* (2013.01); *A61N 1/0496* (2013.01); *A61N 1/36014* (2013.01); *A61N 1/37247* (2013.01)

(58) Field of Classification Search
CPC .. A61N 1/0468; A61N 1/0476; A61N 1/0496; A61N 1/36014; A61N 1/37247; A61N 1/0492
See application file for complete search history.

(56) References Cited

U.S. PATENT DOCUMENTS

| | | | | |
|---|---|---|---|---|
| 2007/0179585 | A1 | 8/2007 | Chandler | |
| 2015/0050234 | A1* | 2/2015 | Athanasiou | A61L 26/0066 424/78.25 |
| 2018/0093106 | A1* | 4/2018 | Binner | A61K 8/345 |
| 2018/0311499 | A1 | 11/2018 | Yun | |
| 2019/0098738 | A1 | 3/2019 | Frame | |
| 2019/0240475 | A1 | 8/2019 | Lawson | |
| 2020/0061379 | A1* | 2/2020 | Bogie | A61F 13/0253 |
| 2021/0128932 | A1* | 5/2021 | McErlean | A61N 5/022 |
| 2021/0290942 | A1 | 9/2021 | Bijelic | |

FOREIGN PATENT DOCUMENTS

| | | | |
|---|---|---|---|
| WO | 2013155193 | 10/2013 | |
| WO | 2019166965 | 9/2019 | |
| WO | WO-2019166965 A1 * | 9/2019 | A61N 1/0408 |

* cited by examiner

*Primary Examiner* — Paula J Stice
(74) *Attorney, Agent, or Firm* — Themis Law

(57) ABSTRACT

A biomedical device for the therapeutic treatment of ulcers or lesions, particularly diabetic ulcers, includes a kit having, in combination, an electro-stimulating device and a dressing with a pharmaceutical composition that are to be applied simultaneously to an ulcer or lesion.

16 Claims, 7 Drawing Sheets

BIOMEDICAL DEVICE FOR THE TREATMENT OF ULCERS OR LESIONS

FIELD OF THE INVENTION

The present invention relates to a biomedical device for the treatment of ulcers or lesions, particularly for the treatment of diabetic ulcers.

BACKGROUND OF THE INVENTION

Diabetes is considered to be the most critical global noncontagious disease. There are several scientific opinions relating to this disease. While there is no doubt that it is a metabolic disorder characterized by hyperglycemia, on the other hand the onset of diabetes is accompanied by other factors, such as obesity and cardiovascular disorders. In any case, this disease provides a significant socio-economic burden since it is a chronic disease, which must be kept under control for the entire life of patients and affects millions of people around the world.

If diagnosed late, due to a delay in the actions to control the glycemic level compared to the time of the onset of the disease, this provides effects that deeply compromise the functionality of the patients' feet and legs, causing severe neuropathic pain, circulation problems and the formation of chronic ulcers in these areas of the body. The progression of all these factors can also lead to the amputation of part of the leg/foot.

Diabetic ulcers are characterized by a chronic inflammatory environment and an altered or interrupted skin regeneration mechanism. These unresolved wounds are a gateway for pathogenic microorganisms due to the lack of skin tissue.

Furthermore, wound exudate is a perfect medium for bacterial proliferation and as a result, the difficult management of the infection makes the treatment of diabetic ulcers a major concern.

The condition of persistent hyperglycemia, typical of diabetes, deeply affects the lower limbs causing circulation problems, poor blood circulation, peripheral neuropathic pain, and loss of skin sensitivity, leading to tissue death (maceration, gangrene).

Pharmacological treatments are known to the state of the art, which include wound dressings, which are designed to control and support the healing of ulcers locally. The dressings are made in the form of films, fibrous mats, sponges and hydrogels for the in situ administration of antibiotics, antioxidant and anti-inflammatory molecules and growth factors. The modern biomaterials used in these dressing devices try, at the same time, to counteract the invasion and proliferation of microorganisms, eliminate free radicals present in the exudate, rebalance the persistent inflammatory condition and promote the proliferation of skin cells in order to achieve proper wound repair.

However, the low scalability, high production cost, local side effects and bacterial resistance still deeply limit the introduction of these technologies. Furthermore, the dressings are not designed to deal with neuropathic pain and the circulation problem related to diabetic ulcers, completely limiting their use to a local application, and making the results, in terms of healing effectiveness, relatively limited also in relation to the therapy duration. The therapeutic process that makes use of this kind of dressings requires interventions by healthcare personnel who, in addition to performing the replacement of the device, also control the evolution of the pathological condition and/or direct interventions on the ulcer itself, such as for instance cleaning, extemporaneous application of further drugs and other actions. However, this requires a constant and cyclical intervention of the healthcare personnel which is not limited to a mere control activity, so that the treatment costs become relatively high.

In the state of the art, biomedical devices for therapeutic applications by electrical stimulation are also known.

In general, these are devices that provide for the emission through the skin, by means of electrodes applied to the skin itself, of electrical impulses configured according to particular sequences and according to particular parameters such as signal power, voltage, current intensity, frequencies and waveforms. They are therefore non-invasive therapeutic biomedical devices that show efficacy in the treatment of neuropathic pain, in the improvement of circulatory flow and in the treatment of vascular disorders related to diabetes as well as in the treatment of skin lesions such as ulcers related to diabetes.

Furthermore, current electrostimulation techniques used in the treatment of diabetic ulcers require a relatively long treatment time, which causes patient discomfort and increases treatment costs.

Particularly, electrostimulation devices operating according to FREMS technology have proved effective both in the treatment of neuropathic pain and in increasing blood flow in the anatomical areas where they are applied. Studies and experiments related to this technology show an ability to increase the release of growth factors such as vascular endothelial growth factor (VEGF), valid for the treatment of diabetic ulcer.

Frequency and amplitude modulated neuronal electrical stimulation or FREMS~ (Frequency Rhythmic Electric Modulation System) is described in documents IT 1341343 (2007), WO2004067087A1, EP1305080 and WO 2004/084988 (incorporated herein by reference) and is characterized by the use of transcutaneous electrical currents, produced by sequential electrical impulses with variable frequency and duration. The frequency can vary from 0.1 to 999 Hz, the duration of the stimulus is between 0.1 and 40 ps and the voltage, constantly maintained above the perceptual threshold, is comprised between 0.1 and 300 V (preferably 150 V).

Particularly, WO 2004/084988 describes a microcirculation activation sequence (ATMC) and a muscle fiber decontracting sequence (DCTR), which are capable of soliciting various functional districts, including striated muscle, smooth muscle and peripheral nervous system. The aforementioned stimulation sequences are based on three fundamental parameters: the duration of the stimulus, the frequency of the stimulus and the time intervals during which different duration/frequency combinations follow one another. The operating general pattern of the stimulation sequences mirrors the digital-to-analogic transduction that occurs in the transmission of a nerve impulse.

Frequency and amplitude modulated neuronal electrical stimulation or FREMS (Frequency Rhythmic Electric Modulation System) described in the aforementioned WO 2004/084988 and in WO 2004/067087 (incorporated herein by reference), is characterized by the use of transcutaneous electrical currents, produced by sequential electrical impulses with variable frequency and duration. The frequency can vary from 0.1 to 999 Hz, the duration of the stimulus is between 0.1 and 40 μs and the voltage, kept constantly above the perceptual threshold, is between 0.1 and 300 V (preferably 150 V). By suitably combining the aforementioned variations in frequency and duration, a specific sequence is obtained, called DCTR, having a decontracting effect and including a series of sub-phases, called A, B and C. Frequency and amplitude are constant in sub-phase A, the frequency is constant and the amplitude variable in sub-phase B, the frequency is variable and the amplitude constant in sub-phase C.

Experimental studies have made it possible to evaluate the effects of FREMS and the ability of the latter to evoke composed muscle action potentials (cMAP), obtainable in the proper adductor muscle of the big toe by stimulating the posterior tibial nerve, as well as the variation in amplitude of the reflex H using the latter as a conditioning stimulus. As described in WO 2004/084988, the aforementioned experimental studies have also shown that the greater amplitude of the cMAPs (0.60±0.02 mV) obtainable is about 15 times lower than that of the cMAPs obtained with the known devices delivering TENS currents, i.e. of the order of 9±0.6 mV with stimuli having a duration typically included in a range of 200-1000 μs. It has also been observed that the maximum amplitude value of the cMAPs is obtained in the presence of a duration/frequency ratio equal to 0.13 (40 μs/29 Hz).

A further kind of sequence, called ATCM and suitably designed to obtain a vasoactive effect, has a prevalent action on the motility of the microcirculation, that is, of the smooth sphincters of the arterioles and venules of the subcutaneous tissue. In practice, as described in WO 2004/084988, a system is obtained which produces a sequence of vasodilatations and vasoconstrictions with sequential increases and decreases in the blood flow of the microcirculation surrounding the stimulation zone. These vasodilatations and vasoconstrictions produce a "pump" effect evidently produced by a neuromodulation of the sympathetic autonomic system, which influences the vasoaction precisely through the smooth muscles of the capillaries and arterioles. In this way it can be seen that this subsequence, characterized by alternating variations of the rheobase, therefore produces a vasoactive effect consisting of phases of vasodilatation and sequential vasoconstriction phases. This certainly also produces a draining effect and, above all, an elasticization of the microcirculation and a modulation of the latter around a main bearing event that determines its average variation.

Despite the aforementioned clinical effects, even the biomedical therapeutic devices operating according to the FREMS technology lack some crucial aspects to support the wound healing process. For instance, this system does not have antibacterial and antifungal properties, cannot guarantee any covering action of the wound and the ability to absorb exudate. Furthermore, investigations regarding the anti-inflammatory effects for FREMS technology have not yet been reported. Therefore, both for devices operating according to Frems technology, and for electrostimulation devices operating according to other stimulation technologies or methodologies, as regards the configuration of the pulse sequences transmitted to the anatomical districts, the effectiveness remains limited and not completely decisive for achieving the healing of ulcers, particularly diabetic ulcers and particularly as regards the healing times and the level of healing of the lesions.

SUMMARY OF THE INVENTION

An aspect of the present invention is therefore that of producing a biomedical device for the treatment of ulcers, particularly for the treatment of diabetic ulcers, which has an improved therapeutic efficacy as regards the times and levels of healing of ulcers and particularly of diabetic ulcers.

A further aspect relates to the production of a biomedical device for the treatment of ulcers and particularly of diabetic ulcers which in combination with an improved therapeutic efficacy presents a greater convenience of application in situ and/or replacement during the therapeutic process and which is also relatively compact, easy to control and use and relatively inexpensive especially with respect to currently known devices.

A further aspect of the present invention consists in the fact that the device is a wearable and temporarily fixable device and therefore fixable and separable from the user's body.

A further aspect of the invention envisages the aim of not having to remove the dressing from the user's body thanks to its reabsorption by the skin once the treatment is finished.

According to a first embodiment, the present invention relates to a biomedical device for the therapeutic treatment of ulcers or lesions, particularly diabetic ulcers, said device consisting of a kit comprising in combination an electrostimulator device and a dressing comprising a pharmaceutical composition, applied simultaneously to an ulcer and wherein the electrostimulator device comprises:

- at least one generator of electrical pulses, said electrical pulses being organized in sequences of electrical pulses having prefixed values of typical parameters, said typical parameters comprising one or more of the following parameters: amplitude, duration, frequency and/or waveform of said pulses and which parameters are configured according to the technology called FREMS;
- said generator comprising at least two separate stimulation channels, through which said sequences are delivered to body areas of an organism independently for each channel;
- at least two stimulation electrodes, each of which is connected or connectable to a respective stimulation channel and each of which is intended to be removably applied to one of two different prefixed body zones of an organism;
- each electrode being applied externally to the patient's skin in correspondence with said prefixed area and with a prefixed position relationship with respect to the position of the at least one further electrode;
- a control unit of said at least one electric pulse generator communicating with said electric pulse generator;
- a command and/or data entry interface for setting and/or displaying setting and/or setting settings data of said one or more generator;
- said dressing being consisting of a film comprising a solution of povidone iodine (PVP-I) and sodium alginate (NaAlg) and intended to be applied to the ulcer;

and wherein

- the at least two electrodes are intended to be arranged on diametrically opposite sides of the lesion at a prefixed distance therefrom.

According to an embodiment, the electric pulses fed to said two electrodes have a different polarity and said polarity of said electrode pulses is inverted at least once or cyclically with respect to said two electrodes after a prefixed period of time.

According to a further embodiment which can be provided in any combination with one or more of the previous embodiments, the expected distance of each electrode from the edge of the ulcerative lesion facing the corresponding electrode is of the order of at least a few centimeters, particularly of at least 1 cm.

As regards the formulation of the aforementioned dressing, an embodiment provides that it can consist of Sodium alginate, PVP-I and glycerol.

Sodium alginate is a natural carbohydrate polymer used in the wound healing process such as known from Varaprasad et al. 2020 “Alginate-based composite materials for wound dressing application: a mini review”; Kurakula et al. 2020 “Chapter 13-Alginate-Based Hydrogel Systems for Drug Delivery in Wound Healing.” However, pure alginate has poor mechanical properties, being a relatively rigid material and limiting its potential application to a different part of the body. For this reason, glycerol was introduced as a plasticizer in the sodium-alginate film, thus obtaining a reduction in Young’s modulus and tensile stress at maximum load and an increase in the elongation capacity of the films.

According to one embodiment, the dressing film can be obtained by adding to a solution comprising sodium alginate with a concentration of 4.6 to 5.2% w/v and PVP-I with a concentration of 1.3 to 1.9% w/v glycerol at a concentration of 1.3 to 2.3 w/w with respect to the total weight of sodium alginate and PVP-I.

This kind of dressing has the advantage of being naturally resorbed, thus avoiding the need for a detachment from the lesion and therefore the possibility of generating new lesions when replacing the dressing. After absorption, in fact, a new dressing can be easily applied simply by superimposing a new dressing film on the lesion and/or possibly what remains of the previous film.

According to one characteristic, the resorption of the dressing by the skin takes place particularly for a thickness of the aforementioned film less than 2000 μm, preferably less than 100, even more preferably from 75 to 95 μm.

As will be seen in more detail also from the experimental results, the combination of electrical stimulation according to a FREMS technology with the dressing using a film obtained from a solution of sodium alginate, povidone iodine and glycerol, allows to obtain a therapeutic effect on the treatment of ulcers, particularly of diabetic ulcers which is surprisingly and unexpectedly, considerably more effective, than the single treatments separated from each other or the simple sum of the therapeutic effects of the single actions of electro stimulation and pharmacological treatment.

This unexpected and surprising increase demonstrates a synergistic effect of the action of electrical stimulation and pharmacological action.

As regards the configuration of the biomedical device in the form of self-medication and therefore to be practically usable also directly by the patient, the present invention provides several advantageous embodiments.

According to an embodiment, said at least two electrodes are each carried by an independent flexible support element, self-adhesive, which can be fixed in a prefixed position in relation to the anatomy of the human body.

According to another embodiment, said at least two electrodes are carried by a single flexible, self-adhesive support element, which can be fixed in a prefixed position in relation to the anatomy of the human body, said flexible element having at least two branches which delimit an area at least of concave shape for housing the lesion, while each said electrode is provided on one end of the respective branch, said concave area being configured to house a dressing film.

According to another embodiment, said flexible element is shaped like a frame 75 closed on itself which has a free central area 78 intended to accommodate the lesion, said at least two electrodes 76 being provided on said frame in two points of the same diametrically opposite each other with respect to the center of said frame, while the dressing consists of a film of such shape and size as to be at least inscribable inside said frame.

Thanks to the aforementioned embodiments, the correct application of the electrodes with respect to the lesion is easy, avoiding leaving too much discretion for the non-specialized user.

Particularly, the embodiment which provides for a frame allows the lesion to be centered with respect to the position of the two electrodes and therefore to always have the electrodes in the most effective position relative to the lesion. The central window defined by the frame not only allows correct the positioning of the electrodes, but also the correct positioning of the dressing film.

In one embodiment, it is also possible to provide a closure layer 77 which overlaps, at least partially, the frame and/or the support branches of the electrodes and also the concave area 78 or the central area, adhering only to the flexible support elements of the electrodes, and therefore to the frame and/or to the two support branches of the electrodes and not exhibiting an adhesive action in correspondence with the lesion and the dressing film. This allows the area of the ulcerative lesion to be further protected and isolated from the external environment, while avoiding direct contact between the layer that covers the lesion area and the lesion itself and therefore the worsening of the lesion upon detachment of said coverage layer.

According to still a further embodiment which can be provided in any combination or sub combination with the previous embodiments, the shape and dimensions of the frame are chosen corresponding to the size, or the extension of the lesion, being provided particularly a series of different frames that have different shapes and also different sizes, particularly of the central free area.

Similarly, the shape and extension of the dressing film are also provided corresponding to the shape and size of the lesion to be treated and therefore of the central free area of the frame.

The frame can have different shapes such as circular, elliptical, ovoid, rectangular, square or polygonal shapes, or even combinations of these shapes made in such a way as to follow the morphology of the anatomical areas of application.

According to a still further feature which can be provided in any combination or sub-combination with the previous features and embodiments, the aforementioned generator, the aforementioned control unit and the aforementioned command and/or display interface and the power source of these components are integrated in a single control device, said device being connected or connectable by means of electric cables to the aforesaid electrodes.

The connection can be fixed, or the connection can be made through coupling terminals provided at the end of the connection cable with the corresponding electrode, which are connected in a separable way to corresponding connection terminals steadily associated with said corresponding electrode.

The aforesaid terminals are known and the person skilled in the art can choose among the existing terminals those which he considers most suitable for the purpose.

Different variants can provide that a cable having substantially a certain prefixed length departs from each output channel of the generator, and a connection terminal, while from the electrode only the corresponding terminal, possibly mounted at the end of a shorter length of cable, departs, with respect to that of the section of cable associated with the generator, or vice versa.

According to an embodiment, the control device is provided in combination with a wearable element for removable fastening of said control device to an anatomical region of the patient.

These wearable elements can be of the mechanical type, such as for instance pockets that can be tightened around limbs such as arms or legs by means of tightening straps and/or elements such as leggings, sleeves or bands that can be tightened around areas of the patient's body or also wearable elements that can be fixed by means of an adhesive action, such as flexible elements like a plaster.

In one embodiment, the aforementioned wearable elements can be provided with lockable and openable housing pockets for said control device.

A particular embodiment can provide the aforementioned wearable elements, in the form of flexible elements in the form of one or more external side extensions of one branch of the at least two branches 73 of the flexible element supporting the electrodes or of the flexible element supporting the shape of the frame.

Another embodiment which is particularly advantageous in combination with the previous feature may provide that the conductors connecting the electrodes to the corresponding channel of the generator are integrated into the structure of the flexible element.

Another embodiment of the aforesaid embodiment can comprise a support element for the control device wherein the connection terminal of the conductors connecting the electrodes to the control device is in the form of a connection base 80 steadily fixed to said flexible element.

In relation to this embodiment, said terminal connection base 80 can be provided inside the aforementioned housing pocket of the control device, or said connection terminal base can provide removable mechanical engagement members to corresponding mechanical engagement elements for the simultaneous electrical and mechanical connection of said control device thus constituting both the electrical connection terminal and the wearable support element for the control device. In the case of this embodiment, said control terminal base can be provided directly on a branch or in a point of the frame, or in the combination of the two branches, for instance an intermediate point between the two electrodes, making unnecessary the provision of an extension of the flexible element for the wearable support of said control device.

An embodiment of the flexible element according to one or more of the embodiments described above may provide that said flexible element comprises multiple layers that are congruent and laminated to each other, wherein:

- at least a first base layer, one of the sides of which is provided with a coating of adhesive material and in the areas coinciding with said at least two electrodes, a coating which favors electrical conduction with the skin;
- a layer superimposed on this first layer which brings said at least two electrodes and the electrical conductors in the form of cables or electrically conductive tracks for connection to the generator, as well as the terminal base for electrical connection to the control device in the prefixed position;
- a finishing layer on the side opposite to that of adhesion to the patient's body.

The biomedical ulcer treatment device can therefore consist of a kit consisting of the combination of at least one flexible support element for two electrodes and supporting at least one control device, said flexible element being shaped so as to delimit a concave zone and/or a window surrounded by a frame closed on itself, as well as at least one element of a film or a plurality of elements of said dressing film having a shape substantially congruent with the area delimited by the flexible support element, of a control device which can be removably applied to said flexible element and optionally to a cover sheet of the concave area and/or said window and can be removably applied to the face opposite the application surface of the flexible element and which overlaps at least partially to said concave area and/or to said window and/or to said control device.

In another embodiment, the control device can steadily integrate a power source which can be of the rechargeable and/or replaceable type, or the control device is a disposable device since the power source is neither replaceable nor rechargeable.

According to still further embodiments, it is possible to provide that the control device has communication interfaces of the wireless kind with which it can communicate with remote units, such as cell phones, remote servers, PCs or other devices configured to perform functions of a simple display interface and/or remote control and/or maintenance functions and/or upgrade functions or other functions that cannot be performed directly from the control device itself.

The invention has further features and improvements that are the subject of the dependent claims.

BRIEF DESCRIPTION OF THE DRAWINGS

These and other characteristics and advantages of the present invention will become clearer from the following description of some embodiments illustrated in the enclosed drawings wherein.

DETAILED DESCRIPTION OF EMBODIMENTS OF THE INVENTION

Figure 10:
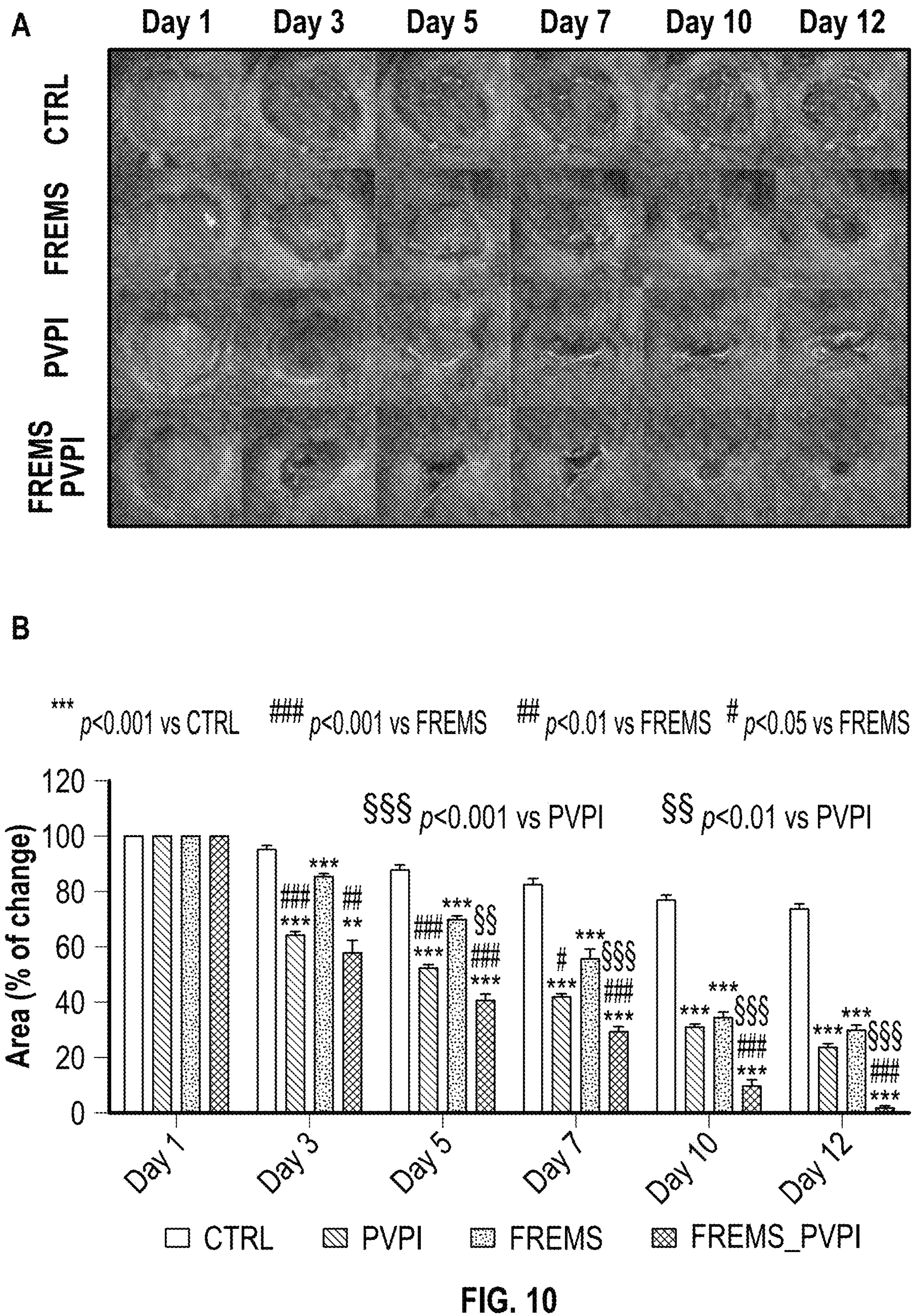
FIG. 10 shows photographs of the lesion area relating to a control group, a group treated with electrostimulation only according to a FREMS technology, a group treated with only PVP-I dressing and a group treated with the combination of electrostimulation according to the technology FREMS in combination with a PVP-I dressing according to the present invention and the graphic representation of the area of the lesion as a function of the days of treatment.
Figure 11:
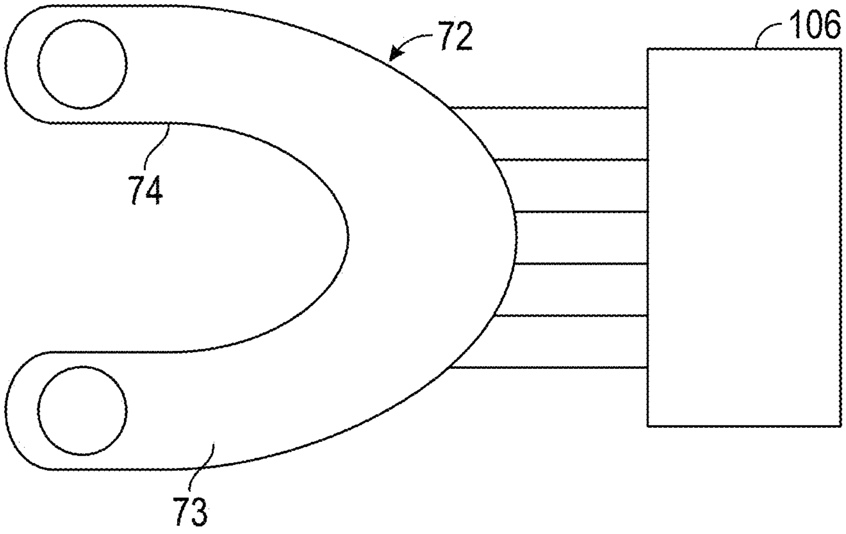
FIG. 11 shows an embodiment having a plurality of branches.
Figure 12:
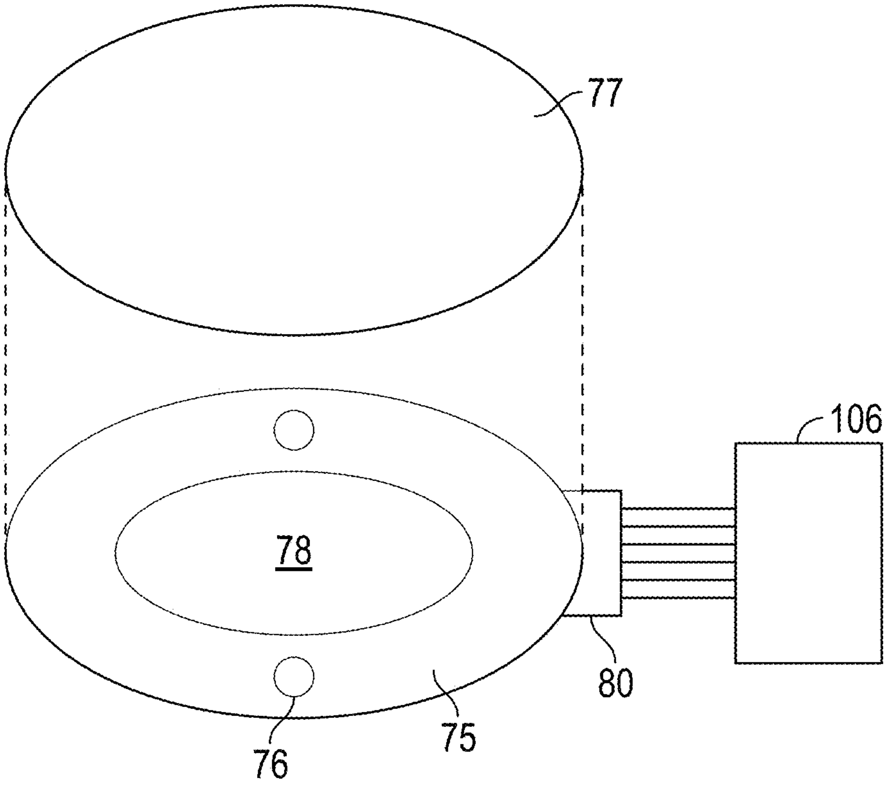
FIG. 12 shows an embodiment made of a flexible element and having a conductor terminal shaped as a connection base and further having a closure layer.

With reference to the more general embodiment of the present invention, the biomedical device for the treatment of ulcers, particularly diabetic ulcers, comprises a pair of electrodes for the transmission of electrostimulation impulses according to a FREMS technology said electrodes being meant to be applied in diametrically opposite positions with respect to the area presenting the lesion, as shown in FIG. 10.

This figure compares the results obtained in the treatment of ulcers caused in diabetic mouse models.

In these experiments, were considered untreated mice, mice treated only with the dressing consisting of a NaAlg/PVP-I film, mice treated only with an electrostimulation according to the FREMS technology and mice treated with a device according to the present invention which provides a pharmacological treatment with a dressing using a NaAlg/PVP-I film and simultaneously with an electrostimulation; the main results of the experiment are reported. As it can be seen, during the monitoring period of 12 days, in the untreated mice, called CTRL, the ulcerative lesion did not substantially undergo any healing due to the diabetic condition, showing at the end of the observation period 80% of the area of the wound still not healed. The application of FREMS technology showed a gradual wound healing during the observation period (12 days) and led to a recovery of 70% of the area initially affected by the wound. The FREMS technology was statistically better than the CTRL controls as also shown in the lower graph in FIG. 10.

Figure 9:
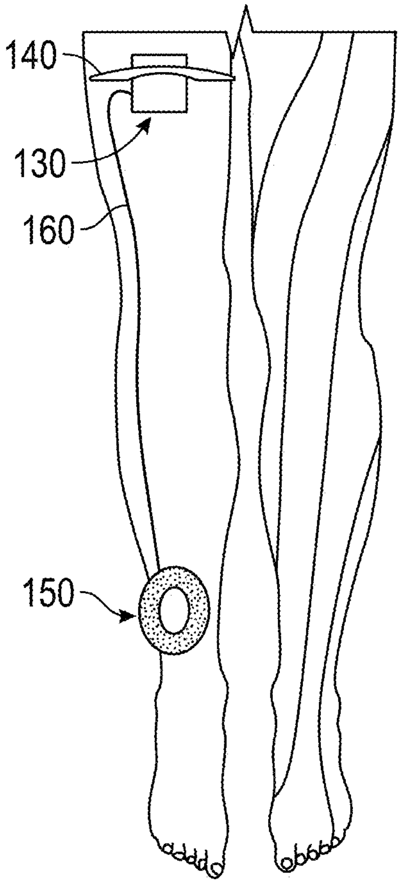

Mice treated with the PVP-I based dressing alone, identified with PVP-I, showed a slight difference in the progression of the wound healing process. In fact, as can be seen in FIG. 9, a first major effect of the healing process was observed both with respect to controls and FREMS technology up to the first 7 days. After 12 days, mice treated with PVP-I based patches showed a residual wound area of 23%, which was statistically better than CTRL.

Finally, mice treated with both wound dressing and FREMS technology showed a surprising synergistic effect of the two therapies. In fact, from the very first days, the condition of the wound was statistically improved both in relation to the CTRL group and in relation to the group treated with electrostimulation only and the group treated with dressing only. It is important to note that after 5 days, the improvement in repair of the area affected by the lesion was statistically better than in mice treated with the PVP-I based patch alone. Finally, after 12 days, the mice treated with the combination of electro-stimulation according to the FREMS technology and the PVP-I dressing showed a complete recovery of the wounds.

According to these data, both NaAlg/PVP-I and FREMS alone were able to accelerate but not complete wound healing, while the combination of NaAlg/PVP-I and FREMS technology was able to heal the induced wound in 12 days, suggesting a positive synergistic effect of the two technologies.

In carrying out the experiment, the dressing film was prepared according to the following example:

A solution of Sodium Alginate was prepared at a concentration of 5% w/v, PVP-I (povidone iodine) at a concentration of 1.5% w/v in a final volume of 10 mL and glycerol at 1.6% w/w with respect to the total weight of alginate and PVP-I. 1 mL of this solution was placed on a 2×2 cm glass square. The glass with the solution was spin-coated at 180 rpm for 1.5 minutes. The resulting transparent films had an average thickness of 86 μm. After manufacturing, the films were punched into small discs with a diameter of 0.6 cm.

The combination of film and FREMS technology was evaluated in in vivo diabetic mouse models. The disease was induced by treating the animals with a dose of 50 mg/kg of Streptozotocin for 5 consecutive days. After a 4-week period, the blood glucose level of the mice was checked and the mice with blood glucose above 300 mg/dL were considered diabetic. Two experimental cycles were performed. In the first cycle, the speed of wound healing was studied by calculating the wound area at different times. The experiment lasted 12 days. In the second cycle, on the other hand, the level of inflammatory mediators was evaluated 5 days after the induction of the wound. In both groups, full-thickness excisional wounds were generated to begin the experiments.

In both experiments, immediately after the production of the wound, dressing films were applied to the wounds, said films being made according to the example described above. The next day, FREMS therapy began, and the mice were subjected to electrostimulation every day until the end of the experiments.

The electrostimulation program called "Traumatic Ulcers" (described in detail in documents IT 1341343, WO2004067087A1, WO2004/084988 and particularly EP1305080) lasting 30 minutes. The voltage was reduced considering the small body size of the mice compared to human applications described in the documents listed above. The voltage was then reduced to 15 V. The pulse sequences according to FREMS technology were applied by means of two adhesive electrodes directly on the shaved backs of the mice, one of the electrodes was positively charged and the other negatively. These electrodes were replaced with new ones each time after use to ensure full contact between the electrodes and the skin of the mice. During the electrostimulation the two electrodes were applied at a distance of 1 cm from the wound and in opposition to each other. Every day the two electrodes were applied in reverse, i.e., their polarity has been inverted.

During the experiments, the patch was applied immediately after the wound was generated. The next day, FREMS treatment began in the aforementioned "Traumatic Ulcers" mode, limiting the voltage to 15V.

Disturbances in blood flow and persistence of inflammatory conditions are the main reasons for unresolved diabetic ulcers. Therefore, the measurement of the level of inflammatory mediators was performed after the application of the two combined technologies.

After 5 days of injury induced damage in the in vivo diabetic mouse model, TNF-α levels were higher in the CTRL control group, while the values in the group of mice treated with FREMS electrostimulation alone, or with the PVP-I dressing alone and in the group of mice treated with the combination of FREMS electrostimulation and PVP-I dressing were statistically lower. Furthermore, in the group treated with the PVP-I dressing only and in the group treated with the combination of FREMS electrostimulation and PVP-I dressing according to the present invention, these values were also statistically lower than the values of the group treated only with electrostimulation according to FREMS technology.

Also the levels of IL-6 in the group of mice treated only with electrical stimulation according to FREMS technology, in the group of mice treated with only the PVP-I dressing and in the group of mice treated with the combination of FREMS electrostimulation and PVP-I dressing were statically reduced compared to the CTRL control group. However, in this case, treatment with the combination of FREMS electrostimulation and PVP-I medication produced the lowest levels of IL-6, being statistically lower even than the values for the group of mice treated with only electrostimulation with FREMS technology and in the group treated with only PVP-I dressing.

A similar trend was also observed for IL-1R values with treatment with the combination of FREMS electrostimulation and PVP-I medication, showing the best results in reducing the level of this inflammatory mediator.

FIGS. 1 to 8 show different embodiments of a biomedical device for the treatment of ulcers, particularly diabetic ulcers according to the more general concept described above.

In the following description, a flexible support element means a sheet or a flattened element to which are applied or wherein are incorporated by lamination of two or more layers or by drowning, constructive parts such as electrodes, conductors for the transmission of signals or pockets for drugs or for electronic circuits.

Furthermore, the flexible support elements described are intended to be provided with a continuous layer of adhesive or with zones for removable fixing to the skin of the human body.

Figure 1:
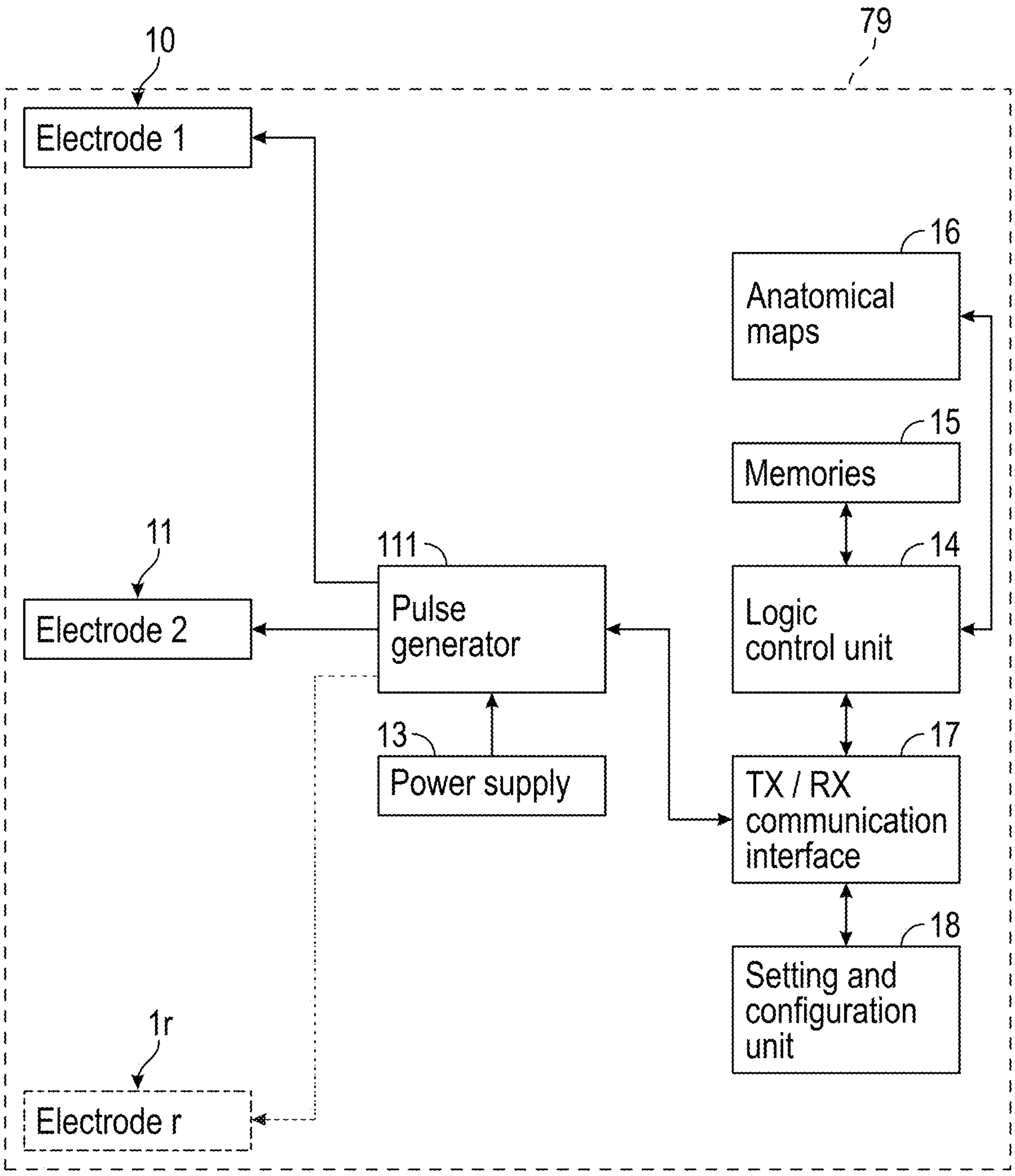
FIG. 1 illustrates a block diagram of an embodiment of the apparatus according to the invention.

FIG. 1 illustrates the block diagram of an electrostimulation apparatus, which according to the present invention is made in the form of a wearable apparatus.

The apparatus comprises one or more flexible supports indicated with 10, 11, 1*r*. Each flexible support bears stimulation electrodes 1, 2, r, the variable r being indicative of any natural number, since the individual supports 10, 11, 1*r* may be provided with an identical or a different number of electrodes. In the embodiment of FIG. 1, the support 1*r* bears an electrode r and is illustrated with broken lines in order to show a possible embodiment which provides for more than two electrodes as provided in the previous experiment and in the preferred embodiment of the present invention.

However, it is possible to optionally provide more than two electrodes, each with its separate flexible element for supporting and adhering to the patient's body in a prefixed area and with a prefixed relative position with respect to the other electrodes.

A generator 111, with an associated power supply 13 has an output channel for each electrode 1, 2, r through which a sequence of electrical stimulation pulses is fed to the corresponding electrode. The pulse generator 111 operates under the control of a logic control unit 14.

This logic control unit is configured to provide the generators with instructions relating to the pulses to be generated in relation to the configuration parameters of said pulses. These parameters are related to one or more of the following quantities: amplitudes, intensity, power, frequency, duration, polarity, waveform and to generate a combination of a temporal succession of different pulses for one or more of the aforementioned parameters as well as to synchronize among them the pulses of the sequences supplied to the electrodes 1, 2, r for their delivery through the skin to the patient.

In the embodiment of FIG. 1, a single logic control unit is provided to control the generator 111 in a synchronized way, but as will appear below, in this case it is a possible embodiment, being possible to provide alternative architectures which provide for two or more control units dedicated to a single generator or to subgroups of generators and which operate in a synchronized way with each other, automatically negotiating the control timing sequences of the generators.

The logic control unit 14 can be made either in the form of dedicated hardware wherein the logic control of the generators is steadily integrated according to one or more options that are selectable but substantially fixed.

Another embodiment, on the other hand, provides that the logic control unit is constituted by generic hardware comprising a processor and peripherals and that the logic control unit 14 executes a control software which is stored in a memory 15. In relation to the specific application of the stimulating apparatus, the memory 15 can contain databases of different settings corresponding to different types of treatment, both as regards the anatomical region and as regards the effects to which the treatment is aimed.

According to a non-limiting embodiment, a memory area 16 can be provided which is dedicated to anatomical maps of positioning of the electrode(s) and/or of the flexible supports 10, 11, 1*r* in relation to the different conditions of the lesions to be treated and/or the anatomical areas wherein they are present.

Always according to a further embodiment which can be provided in any combination with one or more of the embodiments and variants previously described, it is possible to provide a communication interface 17 which allows the control unit to deliver the command signals to the generator 111 and to a setting and configuration unit 18 or to a man-machine interface unit which allows to perform manual maintenance, setting and configuration operations as well as to upgrade the program executed by the logic control unit 14 and/or the databases of the treatment protocols and/or of the anatomical maps of electrode positioning and possibly also of performing diagnostic activities of the units of the apparatus. The communication can take place both by means of cables and by radio, i.e. wireless.

The choice of the communication mode and protocols among those currently known by the skilled in the art is a pure opportunity choice dictated by the required bandwidth, the required signal power, the energy resources provided by the power supply and depends on the kind of architecture of the apparatus and the kind of treatment to be performed.

The setting and configuration unit 18, or the interfacing unit, can consist of a remote unit, such as a mobile device made available to the user. This can also be a mobile device of the kind currently known wherein there is installed an application which when executed configures the mobile device to perform the functions of the interface unit 18 of the apparatus.

Particularly advantageous examples of this kind of mobile unit can be devices such as smartphones, phablets, tablets or similar devices.

A preferred but non-limiting embodiment provides that the generator 11, and all or at least some of the units described above 13, 14, 15, 16, 17 and 18, when present, are integrated in a single control device 79.

In this case, the control unit that integrates all said units or a part of them can consist of a dedicated hardware that incorporates in the hardware itself all the foreseen functions, or said device consists of a generic processing unit which executes a program wherein the instructions are encoded to make such hardware capable of performing the functions required for the execution of the electrostimulation according to the FREMS protocols envisaged in the present invention.

The generator and particularly the control device wherein said generator can be integrated together with one or more of the other units of FIG. 1, can be produced as a wearable device, thanks to a wearable support that can be produced according to different embodiments.

With regard to flexible supports, an embodiment can consist of a support film, for instance of canvas or plastic material, to one of the faces of which a layer of adhesive material is applied. The electrode can consist of a sheet of conductive material cut with a prefixed shape and size and which is applied to the adhesive material. Each pole of each electrode is made from a piece in the form of a sheet of electrically conductive material and a power supply conductor is connected to each pole, for instance in the form of a band of conductive material.

The sheet-shaped pieces of conductive material can be attached to the adhesive layer. The conductors connecting the electrodes to the outputs of the channels of the generator or of the control device can also consist of tracks or bands of a sheet of electrically conductive material, as will be described later.

The electrodes and the conductive tracks or bands are further covered to be electrically insulated towards the outside by a band of plastic material, for instance a double-sided adhesive band, which on one side overlaps the conductors or conductive bands adhering against them and against the adhesive layer of the flexible support, while the other side of the double-sided tape restores the continuity of the adhesive layer in correspondence with the path of the conductors.

Several other construction forms are possible, for instance it is possible to provide that the individual layers are laminated on each other or that the conducting elements are fixed in a plastic matrix by molding. A further embodiment can provide for the production of the poles of the electrodes and/or of the conductive tracks by applying them using electrically conductive liquids which are sprayed to form the poles of the electrodes and/or the conductive tracks of the same.

Figure 2:
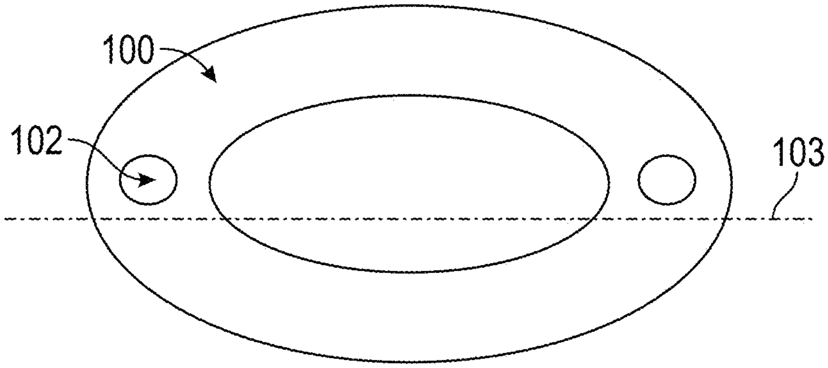
FIGS. 2, 3 and 4 schematically show the three layers of an embodiment of the flexible support for a device according to the present invention.
Figure 3:
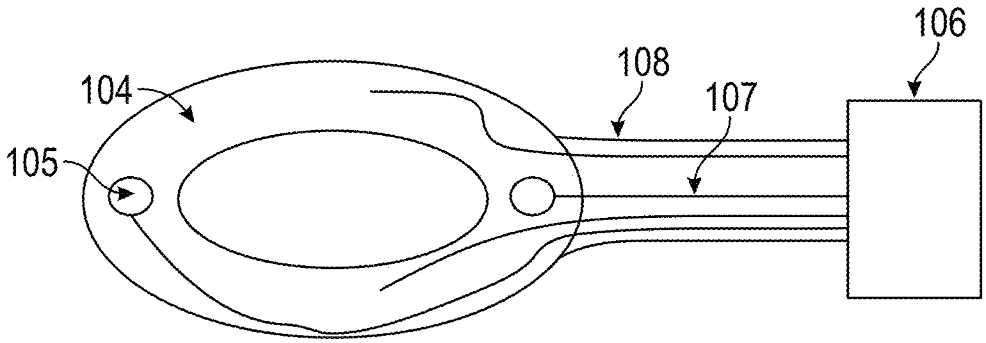
Figure 4:
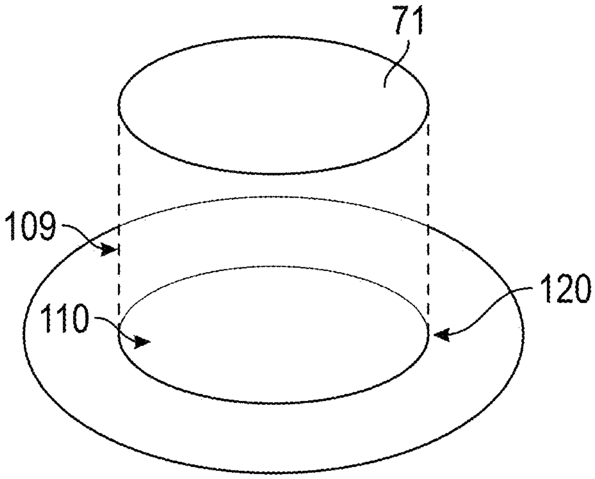

According to an embodiment illustrated in FIGS. 2 to 4, the flexible support for at least two electrodes provided in the preferred embodiment of the present invention is made in the form of a frame that delimits a central window. The frame can be essentially annular in shape which can have any shape such as circular, elliptical, oval, or even polygonal.

On the annular shape it is possible to distribute one or more electrodes 105, in this case two electrodes in diametrically opposite positions.

The flexible element in the shape of an annular frame can bear the connecting conductors of the same integrated inside it as described above, or in the form of electric cables fixed to the external visible surface of said flexible element at least for part of their length to the corresponding generator channel.

The central window is intended to accommodate the lesion or ulcer to be treated, being in this case the dimensions of the frame and/or its shape made so as to form a window of sufficient size to accommodate the lesion and at the same time to determine a position of each electrode relative to the edges of the lesion corresponding to a prefixed optimal distance.

According to one embodiment, this optimal distance is of the order of magnitude of a few centimeters, preferably at least one centimeter. Furthermore, the conformation of the annular frame and the position of the electrodes thereon is such as to make evident the relative positioning of the two electrodes on diametrically opposite sides with respect to the center of the lesion.

A preferred form which allows for easy recognition of the disposition of the electrodes with respect to the lesion is the oblong, particularly elliptical, embodiment shown in the figures, however this embodiment, even if preferred, must not be considered limiting.

As far as the dressing film 71 is concerned, this is made with shape and dimensions substantially corresponding at most to the shape and dimensions of the lesion positioning window delimited by the frame as shown in FIG. 4.

The dressing film made according to one or more of the previously described embodiments is provided as a separate element with respect to the flexible element that bears the electrodes and must be applied in a subsequent step to the application of the flexible element that bears the electrodes.

According to a still further advantageous feature, the flexible support can be made as a multilayer as indicated in FIGS. 2 to 4. In this case, a first layer consists 100 of the flexible support in contact with the skin. This layer is made of biocompatible material, such as preferably polyurethane material.

Said material can advantageously be further permeable to gases and is provided with a layer of adhesive on the part intended to come into contact with the skin.

According to an embodiment, the adhesive is of medium grade.

Still according to a further embodiment, said layer is of transparent material and/or of thin thickness and in any case such as to be sufficiently plastic to allow deformation both in application to the skin and in movement.

The first layer 100 may be have an annular shape and includes special housing areas for adhesion of two electrodes distributed at the two ends of the major axis of the elliptical shape of said first layer 100.

These housing areas consist of Ag—Cl gel and generate contact between the electrode carried by a second layer 104 of the flexible support and the patient's skin.

The second layer 104 of the flexible support is shown in FIG. 3. The second layer may also have an annular shape essentially congruent to that of the first layer 100 and adheres to said first layer by chemical and physical adhesion. The second layer 104 constitutes a non-disposable system of more rigid material, preferably of biocompatible polyurethane.

According to a preferred embodiment, the second layer 104 is also of gas permeable material and includes the circuit part indicated with 107, 108.

Preferably said circuit part is made as a flat cable or in the form of electrically conductive tracks as described above.

The second layer 104 bears, in a position coinciding with the areas 102 of the first layer 100, a corresponding electrode 105 which adheres in contact with the gel of said areas 102.

A control device 106 connects to the conductors 107, 108 and drives the electrodes. The control device 106 can be made according to one or more of the embodiments described with reference to FIG. 1 and can be mounted steadily or in a removable way, for instance in an openable and closable pocket of an adhesive flexible element which has a contact surface with the skin. This flexible support element of the control device 106 is also made of biocompatible material, preferably of biocompatible polyurethane.

According to a preferred embodiment, said material is also adhesive on the surface in contact with the skin.

In combination with the adhesive layer, it is possible to provide a mechanical fixing by tightening thanks to an elastic band, not adhesive such as a band provided with a velcro closure, snap buttons or the like. This band indicated with 140 in FIGS. 7 to 9 has the function of safety fixing of the control unit 106.

Figure 5:
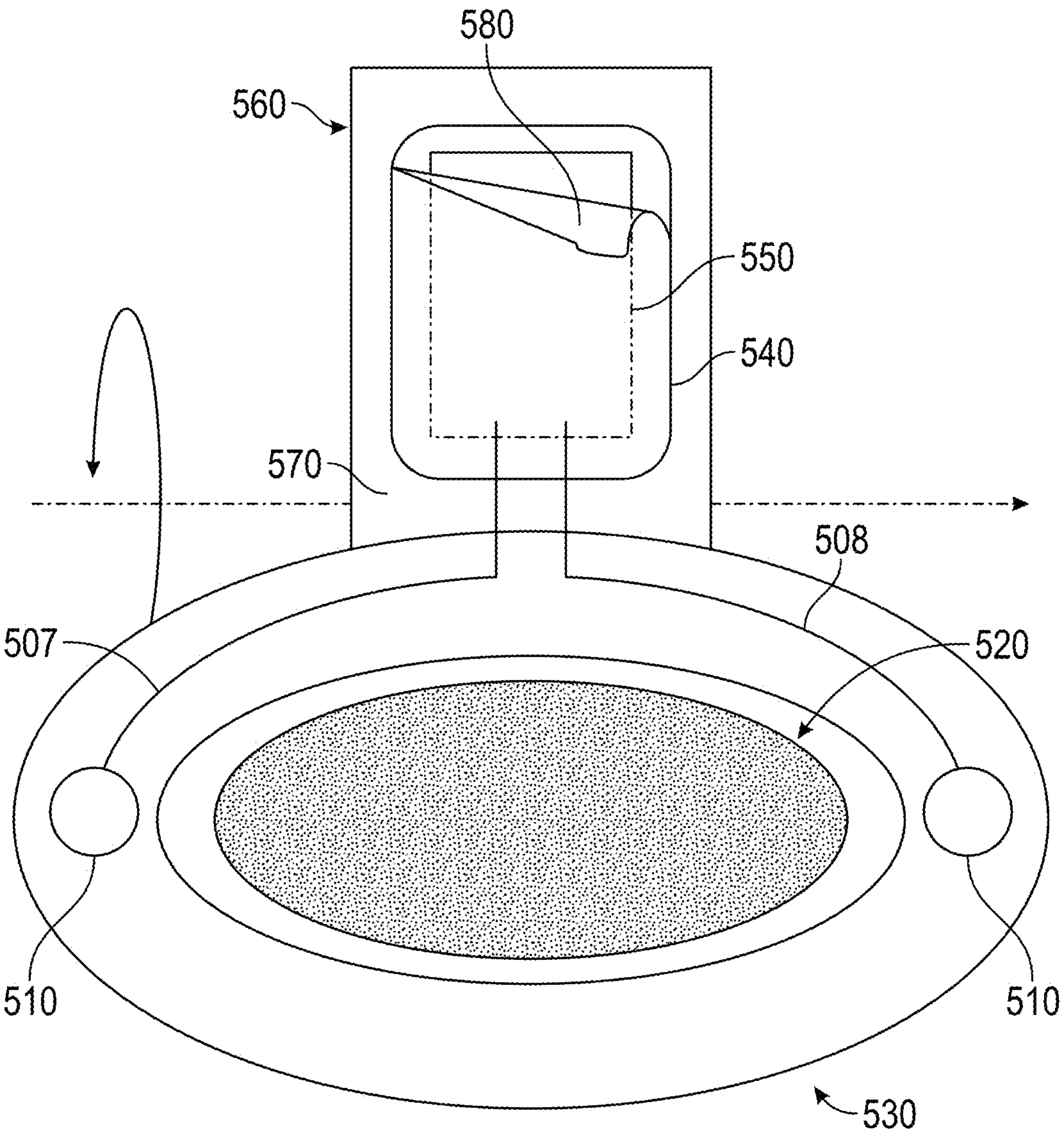
FIG. 5 shows an embodiment of a flexible, adhesive support according to FIGS. 2 to 4 and which further comprises an extension for fixing a control device.

In the embodiment wherein the connection between the electrodes and the corresponding output of the control device is of the conductive band or track kind steadily integrated in the flexible element, the control device 106 is steadily fixed to an extension 560 of the frame 530 as shown in FIG. 5. In this case, in the "not in use" condition, said extension 560 can be foldable against the frame element 530 and can be turned outwards in the condition of application at the moment of use.

The control device indicated with 550 is inserted in a housing pocket 540.

Inside the elliptical element 530, the dressing film applied above the lesion is placed in the window which is centered with respect to said frame element 530 and also provided inside the window.

In a possible embodiment the control device is steadily housed in position between two layers 570 and 580. The conductors 507, 508 are steadily connected to the electrodes 510 and to the corresponding outputs of the control device 550.

In another embodiment, the extension 560 of the flexible element forms an openable pocket so that the control device 550 is removable. In this case, the two conductors 507, 508 can end in a contact base which cooperates with a coupling terminal provided on the control device 550, in such a way that by inserting the same in the pocket, the connection with the control device is automatically generated and extracting the control device from the pocket said contact base is separated from the coupling terminal, interrupting the contact with the electrodes and releasing the control device itself relating to its extraction from the pocket.

Figure 6:
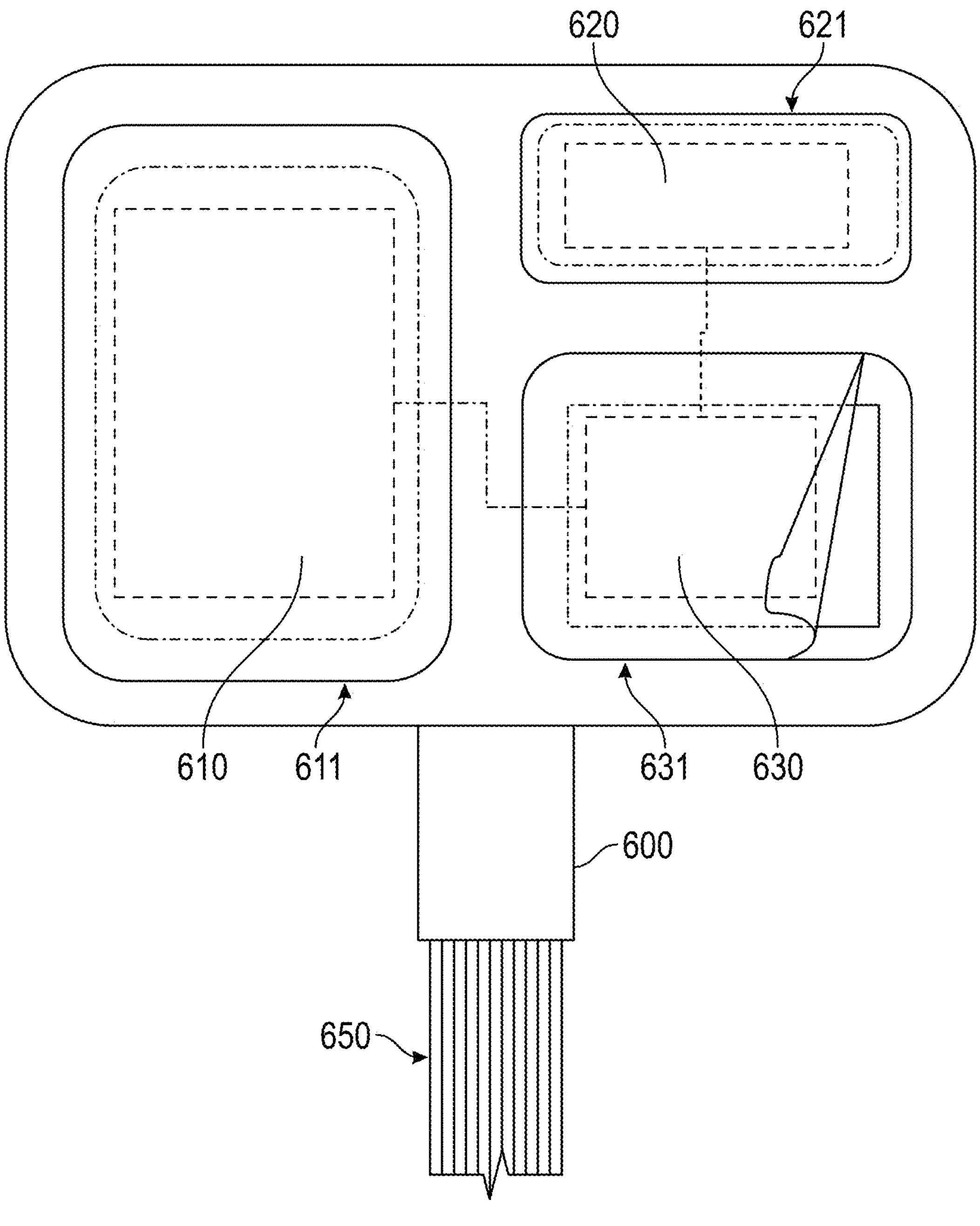
FIG. 6 shows an embodiment of a flexible, adhesive support for a control device and separate battery supply and communication interface with a remote device.

FIG. 6 shows a further embodiment wherein the control device does not integrate all the units referred to in the previous description according to the embodiment of FIG. 1, but these are divided into three separate units, each supported together on a flexible element that can be separated from the flexible element supporting the electrodes or connected to the latter as in the example of FIG. 5.

In this embodiment there is provided a communication unit in transmission and reception 620 and a power supply battery 630 which are separated from the control device 610 which integrates all the other units such as the generator, the control unit, the memories referred to in Example of FIG. 1.

The control device 610, the communication unit 620, the battery 630 are housed in a corresponding pocket 611, 621 and 631 respectively.

As illustrated, at least the pocket 631 of the supply battery 630 can be opened to allow it to be replaced with a charged battery.

Alternatively, one or more of the additional pockets can be opened or the battery pocket cannot be opened, but the battery is of the rechargeable kind and has an externally accessible connection socket with a recharging power supply or recharging can be performed using wireless chargers.

In one embodiment, this battery socket can be accessed through a window (not shown) in the wall of pocket 631 which can be openable and closable or always open.

The pockets 611, 621 and 631 are provided for instance on a flexible support element 600, for instance of the adhesive kind such as those carrying the electrodes.

FIG. 6 illustrates a variant wherein the connection of the control device 610 with the electrodes is made by means of independent electrical conductors for each electrode and which are indicated with 650.

Said conductors extend up to the connection connectors of the generators present on each support element for the electrodes and bear corresponding connection pins.

The connection among control device 610, communication unit 620 and battery 630 can take place through conductive tracks or cables, particularly flat cables, integrated in the flexible element 600.

With reference to FIG. 4, here there is illustrated a further variant of the embodiment, wherein in addition to the first and second layers of FIGS. 2 and 3, said embodiment has a third layer indicated as 109 in FIG. 4.

According to an embodiment, this third layer is of disposable material and has the function of covering the second layer shown in FIG. 3 towards the outside.

According to a further characteristic, the third layer can further cover also the central area of the annular shape of the two underlying layers, extending also along said central part.

Advantageously, the central part is retained by the thickness of the two underlying layers lifted up with respect to the skin and in the part coinciding with the window and is free of adhesive so as not to adhere to the part of the lesion or to the dressing film.

According to yet another embodiment, the third layer 109 can act as an element for closing and opening said central zone of the annular shape of the underlying layers. Said central window indicated with 110 being intended to receive the lesion to be treated and the dressing film.

In an embodiment, on one side of said central zone, the third layer is provided or is shaped in such a way as to form a hinge as indicated schematically by line 120. Said hinge is advantageously elastic and has the function of allowing repeated opening and closing actions, for instance to allow the replacement of the dressing film or the like.

According to a preferred embodiment, the material of the third layer has a greater rigidity than the first layer and is in any case made of biocompatible and/or gas-permeable material.

According to another embodiment, it is possible to provide that inside the window delimited by the frame there can be provided a removable layer of biocompatible polyurethane sponge which has a prefixed thickness and has a prefixed capacity to absorb liquids, particularly for the removal of the exudate by periodic replacement.

With reference to another embodiment that can be derived from that according to FIGS. 2 to 4, in place of a frame closed on itself, it is possible to provide a flexible element which is provided with two branches 73 connected to each other and which form a concave area 74 intended to accommodate the wound and the dressing film. The two branches may be part of a self-adhesive support element 72.

The electrodes are provided at the terminal ends of the two branches 73 which are curved or slanted with respect to each other and have a length such that said ends that bear the electrodes are diametrically opposite with respect to the central bisector axis of the concavity.

With reference to the specific embodiment of FIGS. 2 to 4, it is possible to provide that the flexible element ends at the level of the section line indicated with 103.

Figure 7:
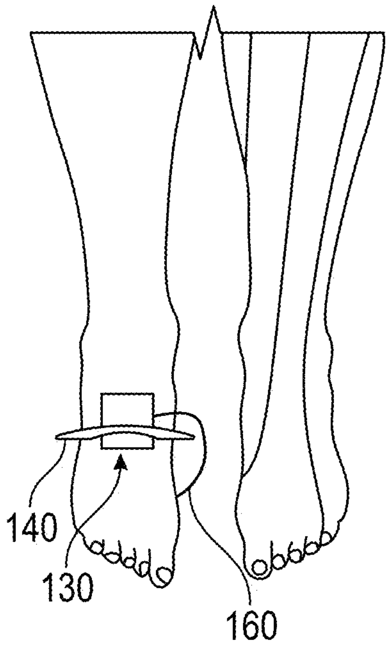
FIGS. 7 to 9 show different embodiments for the wearable application of a device according to the present invention.
Figure 8:
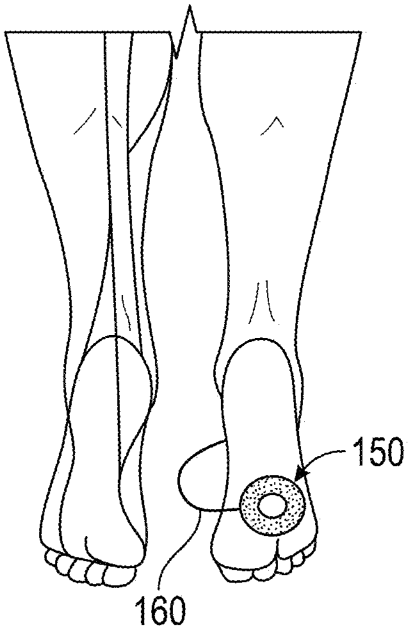

FIGS. 7 to 9 show three examples of application of the apparatus described in FIGS. 2 to 4.

130 indicates the control unit and 140 indicates the fastening by tightening element. 150 indicates the flexible support composed of the three layers of the example of FIGS. 2 to 4.

160 indicates the connection conductors of the control unit 130 to the electrodes of the flexible support according to FIGS. 2 to 4.

The lesion is placed inside the window of the flexible element in the shape of a frame and the dressing film is applied to it.

The invention claimed is:

1. A biomedical device for therapeutic treatment of lesions, said device consisting of a kit comprising in combination an electro-stimulating device and a dressing comprising a pharmaceutical composition, wherein the electro-stimulating device and the dressing are to be applied simultaneously to a lesion, the biomedical device comprising:

an electrical pulse generator, said electrical pulses being generated in sequences of electrical pulses having prefixed values of typical parameters, said typical parameters comprising one or more of the following parameters: amplitude, duration, frequency, or waveform of said electrical pulses, said typical parameters being electrostimulation parameters according to a Frequency Rhythmic Electric Modulation System (FREMS), wherein the generator comprises a plurality of separate stimulation channels, through which said sequences are delivered to a body area of an organism independently for each stimulation channel;

a plurality of stimulation electrodes, each of the stimulation electrodes being connected or connectable to a respective stimulation channel, each of the stimulation electrodes being configured to be removably applied externally to a patient's skin at one of two different predetermined body areas of the organism, wherein each electrode is configured to be applied at a location laterally offset from said lesion and at a distance therefrom, such that no stimulation electrode overlies or contacts said lesion or said dressing applied thereto;

a flexible support element configured to be applied to said patient's skin, the flexible support element being configured as a planar structure carrying the plurality of stimulation electrodes and shaped to define a central concave region dimensioned to house said lesion, so that the flexible support element does not directly contact said lesion;

a control unit of said electrical pulse generator communicating with said electrical pulse generator;

a communication interface for setting data and/or settings of said electrical pulse generator, wherein said dressing consists of a film comprising a solution of povidone iodine (PVP-I) and sodium alginate (NaAlg) and is configured to be positioned withing said central concave region and applied to the lesion, and wherein the plurality of stimulation electrodes are arranged on the flexible support element so as to be positioned diametrically opposite sides of the lesion.

2. The device according to claim 1, wherein a distance between a position of each electrode when applied to the patient's body and an edge of the lesion facing a corresponding electrode is at least 1 cm.

3. The biomedical device according to claim 1, wherein the dressing consists of a solution of Sodium Alginate, PVP-I, and glycerol.

4. The biomedical device according to claim 1, wherein the dressing consists of a film obtained by adding to a solution comprising sodium alginate with a concentration of 4.6 to 5.2% w/v and PVP-I with a concentration of 1.3 to 1.9% w/v and glycerol at a concentration of 1.3 to 2.3 w/w with respect to a total weight of sodium alginate and PVP-I.

5. The biomedical device according to claim 1, wherein the plurality of electrodes are each supported by an independent flexible self-adhesive layer, which can be fixed in a predetermined position in relation to an anatomy of the patient's body.

6. The biomedical device according to claim 5, wherein the electrical pulse generator, the control unit, a power source of the electrical pulse generator, the control unit, and the communication interface, are integrated in a single control device.

7. The biomedical device according to claim 6, wherein the control device is provided in combination with a wearable element for removable fastening of said control device to an anatomical region of the patient's body.

8. The biomedical device according to claim 7, wherein said wearable element is provided with closable and openable housing pockets for said control device.

9. The biomedical device according to claim 7, wherein said wearable element has a foldable side extension, the control unit being fixed to the foldable side extension.

10. The biomedical device according to claim 6, wherein the control device has a terminal for connecting conductors connecting the plurality of electrodes to the control device, the terminal being configured as a connection base steadily to said flexible support element.

11. The biomedical device according to claim 6, wherein said flexible support element comprises at least one dressing film or a plurality of elements of a dressing film having a shape corresponding to the central concave region, and wherein the control device is removably applicable to said flexible support element.

12. The biomedical device according to claim 5, the biomedical device being configured to support the control unit; and at least one dressing film.

13. The biomedical device according to claim 1, wherein said flexible support element comprises and adhesive layer and has at least two branches which delimit the central concave region, said electrodes being each provided on one end of a respective branch, said concave region being configured to house a dressing film.

14. The biomedical device according to claim 1, wherein said flexible support element is shaped like a frame closed on itself which has a free central area configured to accommodate the lesion, said plurality of electrodes being provided on said support element in two points thereof that are diametrically opposite each other with respect to a center of said support element, and wherein the dressing consists of a film of such shape and size as to be at least inscribable inside said central concave region.

15. The biomedical device according to claim 14, further comprising a closure layer shaped to overlay, at least partially, the flexible support element and the central concave region, adhering only to the flexible support element without any adhesive action on lesion and the dressing.

16. The biomedical device according to claim 1, wherein conductors connecting each of the plurality of electrodes to a corresponding stimulation channel of the electrical pulse generator are integrated into a structure of the flexible support element.

* * * * *